(12) United States Patent
Matsumiya et al.

(10) Patent No.: US 10,190,996 B2
(45) Date of Patent: Jan. 29, 2019

(54) METHOD AND DEVICE FOR CONTROLLING ROTARY TABLE

(71) Applicant: MITUTOYO CORPORATION, Kanagawa (JP)

(72) Inventors: Sadayuki Matsumiya, Kanagawa (JP); Hidemitsu Asano, Kanagawa (JP); Masato Kon, Kanagawa (JP)

(73) Assignee: MITUTOYO CORPORATION, Kanagawa (JP)

( * ) Notice: Subject to any disclaimer, the term of this patent is extended or adjusted under 35 U.S.C. 154(b) by 0 days.

(21) Appl. No.: 15/093,134

(22) Filed: Apr. 7, 2016

(65) Prior Publication Data

US 2016/0305894 A1 Oct. 20, 2016

(30) Foreign Application Priority Data

Apr. 17, 2015 (JP) .................. 2015-085352

(51) Int. Cl.
*B65G 47/244* (2006.01)
*G01N 23/046* (2018.01)

(52) U.S. Cl.
CPC ..... *G01N 23/046* (2013.01); *G01N 2223/309* (2013.01); *G01N 2223/3306* (2013.01); *G01N 2223/3308* (2013.01)

(58) Field of Classification Search
CPC .... B65G 47/244; G01N 23/02; G01N 23/046; G01M 1/14
(Continued)

(56) References Cited

U.S. PATENT DOCUMENTS

| 4,969,110 A * | 11/1990 | Little | G01N 23/046 348/26 |
| 5,373,222 A * | 12/1994 | Hemmerle | G01B 11/26 318/572 |

(Continued)

FOREIGN PATENT DOCUMENTS

| JP | 2001-035433 A | 2/2001 |
| JP | 2002-310943 | 10/2002 |

(Continued)

OTHER PUBLICATIONS

U.S. Appl. No. 15/062,571 to Madoka Yasuno, filed Mar. 7, 2016.
(Continued)

*Primary Examiner* — Joseph A Dillon, Jr.
(74) *Attorney, Agent, or Firm* — Greenblum & Bernstein, P.L.C.

(57) ABSTRACT

An XY shift mechanism can shift a rotary table in a two-dimensional direction (XY direction) orthogonal to a rotation axis of the rotary table. By collaborative control of the shift position of the rotary table in the two-dimensional direction in synchronization with the rotation of the rotary table, rotation is made possible about a virtual rotation center that is set at an arbitrary position on the rotary table. The collaborative control of the shift position of the rotary table in the two-dimensional direction also corrects rotation eccentricity owing to the eccentricity of the rotary table. Thus, the virtual rotation center can be set at an arbitrary position on the rotary table, thus enabling obtainment of high resolution tomographic images of a plurality of regions of interest of an object, without the need for repositioning of the object.

1 Claim, 6 Drawing Sheets

(58) Field of Classification Search
USPC .................. 414/757; 382/131; 73/461, 487
See application file for complete search history.

(56) References Cited

U.S. PATENT DOCUMENTS

| | | | | |
|---|---|---|---|---|
| 6,139,183 | A * | 10/2000 | Graumann | A61B 6/4441 378/198 |
| 6,444,991 | B1 | 9/2002 | Yamada et al. | |
| 6,748,806 | B2 * | 6/2004 | Halsmer | A61B 6/4441 378/162 |
| 7,462,011 | B2 * | 12/2008 | Yamazaki | H01L 21/67069 118/500 |
| 8,066,102 | B2 * | 11/2011 | Luo | G01N 23/046 187/267 |
| 8,824,759 | B2 * | 9/2014 | Liu | G06T 11/008 345/424 |
| 9,335,143 | B2 * | 5/2016 | Noda | G01B 21/042 |
| 2003/0159508 | A1 * | 8/2003 | Halsmer | A61B 6/4441 73/462 |
| 2007/0114428 | A1 * | 5/2007 | Yoshino | G01N 23/046 250/370.09 |
| 2008/0217559 | A1 * | 9/2008 | Poglitsch | G01N 23/046 250/491.1 |
| 2010/0118027 | A1 * | 5/2010 | Weiss | A61B 6/032 345/419 |
| 2013/0202180 | A1 * | 8/2013 | Kubo | H01J 37/20 382/132 |
| 2013/0310962 | A1 * | 11/2013 | Noda | G01B 21/04 700/97 |
| 2014/0025336 | A1 * | 1/2014 | Noda | G01B 21/042 702/168 |
| 2014/0037055 | A1 * | 2/2014 | Ogura | H01J 35/08 378/51 |
| 2014/0117251 | A1 | 5/2014 | Momoi et al. | |
| 2014/0130363 | A1 * | 5/2014 | Hagino | G01B 5/22 33/503 |
| 2014/0207419 | A1 * | 7/2014 | Messinger | G01N 27/90 703/1 |
| 2015/0052768 | A1 * | 2/2015 | Wimmer | G01B 21/042 33/503 |
| 2015/0052770 | A1 * | 2/2015 | Noda | G01B 21/042 33/503 |
| 2015/0185107 | A1 * | 7/2015 | Lou | G01N 23/046 73/468 |
| 2016/0133031 | A1 * | 5/2016 | Keyaki | G06T 11/005 378/20 |
| 2016/0265912 | A1 * | 9/2016 | Yasuno | G01B 3/30 |
| 2017/0100760 | A1 * | 4/2017 | Hahn | B21D 22/022 |

FOREIGN PATENT DOCUMENTS

| | | |
|---|---|---|
| JP | 2006-242611 | 9/2006 |
| JP | 2010-523950 | 7/2010 |
| JP | 2012-256516 A | 12/2012 |
| JP | 2014-134528 | 7/2014 |
| WO | 2008/119555 | 10/2008 |

OTHER PUBLICATIONS

Office Action issued in Japan family member Patent Appl. No. 2015-085352, dated Oct. 11, 2018, along with an English translation thereof.

* cited by examiner

Fig. 8

ECCENTRICITY CORRECTION TABLE

| $\phi$ [deg] | $r_\phi$ [mm] |
|---|---|
| 0 | 0.00321 |
| 10 | 0.00158 |
| ... | ... |
| 350 | 0.00209 |

METHOD AND DEVICE FOR CONTROLLING ROTARY TABLE

CROSS-REFERENCE TO RELATED APPLICATION

The disclosure of Japanese Patent Application No. 2015-085352 filed on Apr. 17, 2015 including specifications, drawings and claims is incorporated herein by reference in its entirety.

TECHNICAL FIELD

The present invention relates to a method and a device for controlling a rotary table, and specifically relates to a method and a device for controlling a rotary table that are suitably used in a three-dimensional measurement X-ray CT apparatus and capable of setting a virtual rotation center at an arbitrary position on the rotary table.

BACKGROUND ART

As described in Japanese Patent Application Laid-Open Nos. 2002-310943, 2014-134528, and 2006-242611 and Japanese Translation of PCT Patent Application Publication No. 2010-523950 (hereinafter called Patent Literatures 1 to 4, respectively), three-dimensional measurement X-ray CT apparatuses, which obtain tomographic images of objects in nondestructive manner, are known. As shown in FIGS. 1A and 1B, such a general three-dimensional measurement X-ray CT apparatus includes an X-ray tube (X-ray source 12) for producing X-rays, a rotary table 16 for rotating an object 10 mounted thereon, and an X-ray detector 14 for detecting the X-rays to capture radiographic images of the object 10. The three-dimensional measurement X-ray CT apparatus performs a CT scan in which while the rotary table 16 rotates the object 10, the X-ray source 12 emits the X-rays, and the X-ray detector 14 detects the X-rays to capture the radiographic images of the object 10. The radiographic images are reconstructed to produce a tomographic image of the object 10.

To obtain the tomographic image of the object 10, the CT scan and the image reconstruction are performed. In the CT scan, the object 10 situated on the rotary table 16 is rotated continuously at a constant speed or intermittently at a constant step width, while being irradiated with the X-rays, so that the radiographic images of the object 10 are captured in an entire circumferential direction. The radiographic images of the object 10 captured in the entire circumferential direction are reconstructed into the tomographic image of the object 10 using a reconstruction algorithm such as a back projection method and a successive approximation method.

To obtain a high resolution tomographic image of the object 10 having short sampling intervals, the object 10 during the rotation is required to be projected largely onto the X-ray detector 14 in the CT scan. Thus, in general, as shown in FIG. 2, the object 10 is situated at the rotation center of the rotary table 16, and the rotary table 16 is brought near the X-ray source 12 along an X axis to scale up the radiographic images. In this situation, the object 10 has to be manually repositioned whenever changing a region of interest, unless a specific unit is provided to adjust the position of the object 10.

However, the rotary table 16, together with the X-ray source 12 and the X-ray detector 14, is installed in an X-ray shield room that shields the X-rays. The repositioning of the object 10 requires much time and effort, owing to operations for X-ray emission control to prevent X-ray exposure of an operator, interlock control to open and lock the X-ray shield room, and the like, thus deteriorating operation efficiency. The same goes in situations that obtain a partially enlarged tomographic image of the object 10. A region of interest of the object 10 is required to be positioned at the center of the rotary table 16.

Note that, some of the three-dimensional measurement X-ray CT apparatuses have an XY shift mechanism on the rotary table to adjust the position of the object, as described in Patent Literatures 1 and 2.

However, the provision of the XY shift mechanism complicates the structure of the apparatus, and increases manufacturing costs.

Patent Literatures 3 and 4 describe the provision of an XY shift mechanism under the rotary table, but do not conceive of a rotation center set at an arbitrary position on the rotary table, as in the present invention.

SUMMARY OF INVENTION

The present invention has been made in order to solve the above-described problems in the conventional technique, and an object thereof is to allow the apparatus to set a virtual rotation center at an arbitrary position on a rotary table.

To achieve the above-described object, according to the present invention, a method for controlling a rotary table for rotating an object disposed on the rotary table includes the steps of:

shifting the rotary table in a two-dimensional direction orthogonal to a rotation axis of the rotary table; and performing collaborative control of a shift position of the rotary table in the two-dimensional direction in synchronization with rotation of the rotary table, wherein rotation is made possible about a virtual rotation center that is set at an arbitrary position on the rotary table.

In the step of performing the collaborative control of the shift position of the rotary table in the two-dimensional direction, rotation eccentricity owing to eccentricity of the rotary table may be also corrected.

The rotary table may be intermittently rotated by a minute angle.

When coordinates (a, b) of a position that is set as a rotation center of the rotary table are represented by $a = L \cos \theta$ and $b = L \sin \theta$ and the rotation center (a, b) is moved to a new position (a', b') with rotation of $\Delta\theta$, "a" is shifted by $L \cos(\theta+\Delta\theta) - L \cos \theta$ and "b" is shifted by $L \sin(\theta+\Delta\theta) - L \sin \theta$ in order to bring the new position (a', b') back to the original position (a, b).

The rotation may be continuous.

A destination $C_\theta$ of the center of the rotary table is calculated from the center $C_0$ of the rotary table, a virtual rotation axis, and a rotation angle, and the center $C_0$ of the rotary table may be shifted to the destination $C_\theta$ by the collaborative control of rotary table shift axes, while the rotary table is rotated by the rotation angle $\theta$.

An eccentricity correction table may be produced in advance. The destination of the center of the rotary table may be calculated, and an eccentric amount may be interpolated in the eccentricity correction table to calculate an eccentric amount of the rotation angle. Then, a correction amount may be calculated from the eccentric amount. The destination of the center of the rotary table may be corrected on the eccentricity, and a center $C_{\theta'}$ of the rotary table after the correction may be calculated. By the collaborative control of the rotary table shift axes, the center of the rotary table may be shifted to the center $C_{\theta'}$, while the rotary table is rotated by the rotation angle $\theta$.

According to the present invention, a device for controlling a rotary table for rotating an object disposed on the rotary table includes:

a mechanism for shifting the rotary table in a two-dimensional direction orthogonal to a rotation axis of the rotary table; and a control unit for performing collaborative control of a shift position of the rotary table in the two-dimensional direction in synchronization with rotation of the rotary table, wherein rotation is made possible about a virtual rotation center that is set at an arbitrary position on the rotary table.

The control unit for performing the collaborative control of the shift position of the rotary table in the two-dimensional direction may include a circuit for correcting rotation eccentricity owing to eccentricity of the rotary table.

According to the present invention, the virtual rotation center can be set at an arbitrary position on the rotary table. This enables obtainment of high resolution tomographic images of a plurality of regions of interest of the object, without the need for repositioning of the object. It is also possible to correct the eccentricity of the rotary table.

These and other novel features and advantages of the present invention will become apparent from the following detailed description of preferred embodiments.

BRIEF DESCRIPTION OF DRAWINGS

The preferred embodiments will be described with reference to the drawings, wherein like elements have been denoted throughout the figures with like reference numerals, and wherein:

FIG. 8 is a drawing showing an example of an eccentricity correction table according to the embodiment.

DESCRIPTION OF EMBODIMENTS

An embodiment of the present invention will be described below in detail with reference to the drawings. It is noted that the present invention is not limited to the contents of the following embodiments and examples of the present invention. Components of the following embodiments and examples include those that a person skilled in the art can easily conceive of and that are substantially the same, that is, those within the equivalent scope of the present invention.

Moreover, the components disclosed in the following embodiments and examples can be appropriately combined or selected for use.

Figure 1A:
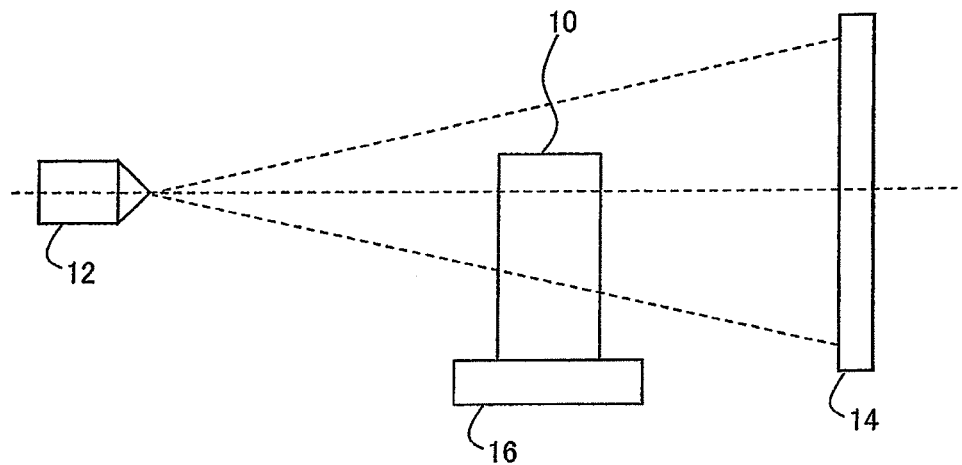
FIG. 1A is a front view showing the essential structure of a conventional three-dimensional measurement X-ray CT apparatus.
Figure 1B:
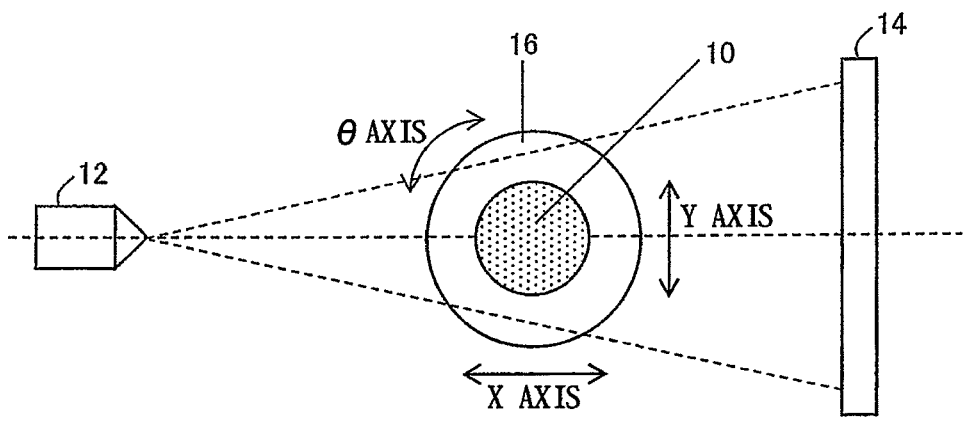
FIG. 1B is a plan view of the same.
Figure 2:
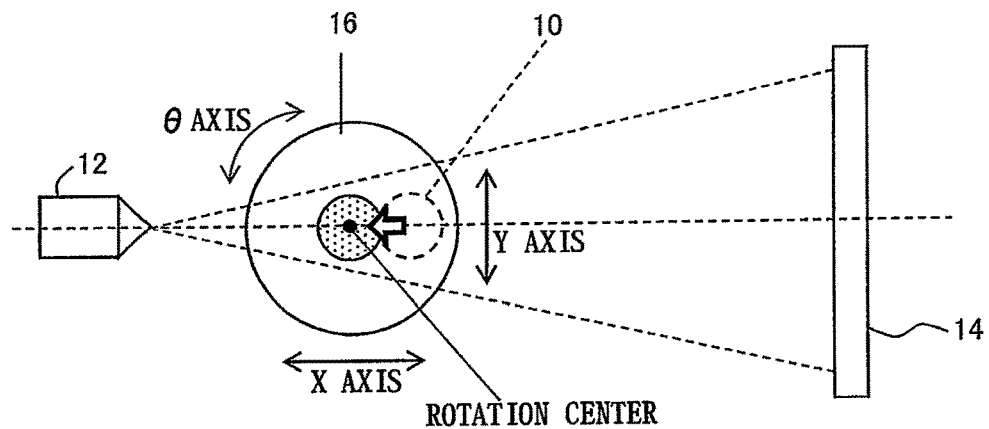
FIG. 2 is a plan view for explaining problems of the conventional three-dimensional measurement X-ray CT apparatus.
Figure 3:
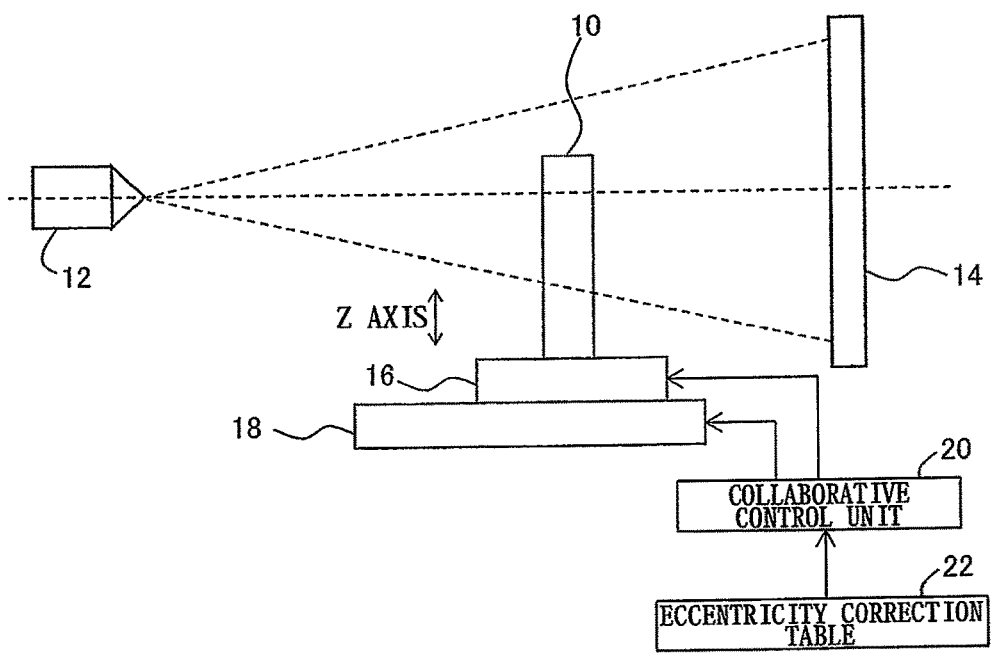
FIG. 3 is a front view showing the essential structure of an embodiment of a three-dimensional measurement X-ray CT apparatus according to the present invention.
Figure 4:
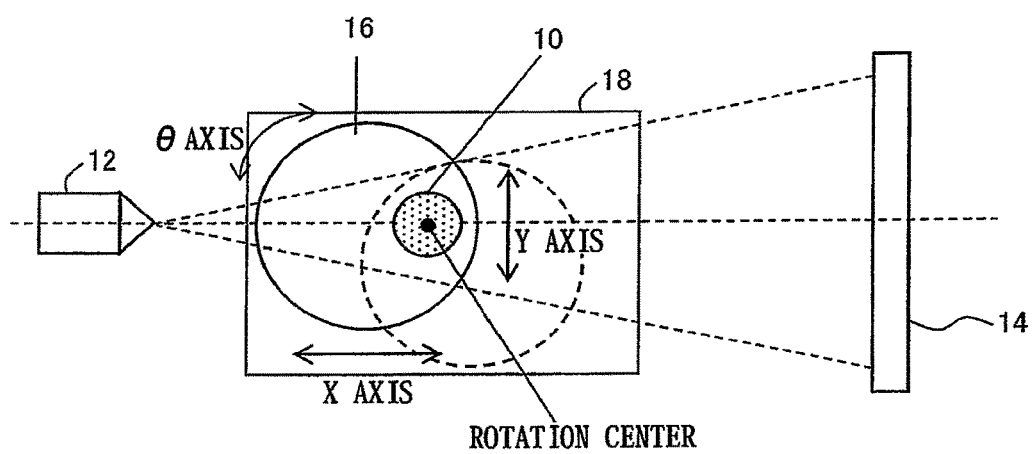
FIG. 4 is a plan view of an operating situation of the embodiment.

FIG. 3 shows the essential structure of a control device for a rotary table in a three-dimensional measurement X-ray CT apparatus to which the present invention is applied. In the three-dimensional measurement X-ray CT apparatus having an X-ray source 12, an X-ray detector 14, and a rotary table 16, this embodiment includes an XY shift mechanism 18 for shifting the rotary table 16 in a two-dimensional direction (XY direction) orthogonal to a rotation axis of the rotary table 16, a collaborative control unit 20 for performing collaborative control of the shift position of the rotary table 16 in the XY direction in synchronization with the rotation of the rotary table 16, and an eccentricity correction table 22 for correcting rotation eccentricity owing to the eccentricity of the rotary table 16, when the collaborative control unit 20 performs the collaborative control of the shift position in the XY direction.

The rotary table 16 adjusts the position and orientation of the object 10 along an X axis, a Y axis, and a $\theta$ axis in conjunction with the operation of the XY shift mechanism 18. The adjustment brings about a variation in a radiographic image captured by the X-ray detector 14. Furthermore, the object 10 is shiftable in height by a not-shown Z axis shift mechanism.

The operation will be described below.

When performing a CT scan of the object 10 situated at an arbitrary position on the rotary table 16, an operator designates a region of interest of the object 10 using an entire tomographic image of the identical object obtained in advance, a video image of the object viewed from the top, or another method.

The center of the region of interest designated by the operator is set as a rotation center. The X axis, the Y axis, and the $\theta$ axis are collaboratively controlled so as to rotate the rotary table 16 about the position of the rotation center.

Figure 5A:
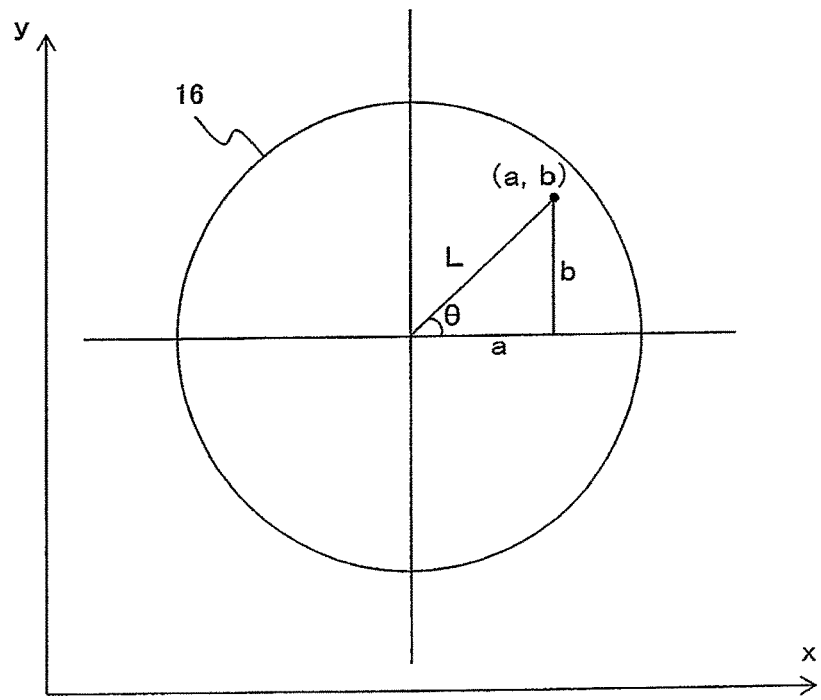
FIGS. 5A and 5B are schematic views showing a control method in a case where the embodiment performs intermittent rotation.
Figure 5B:
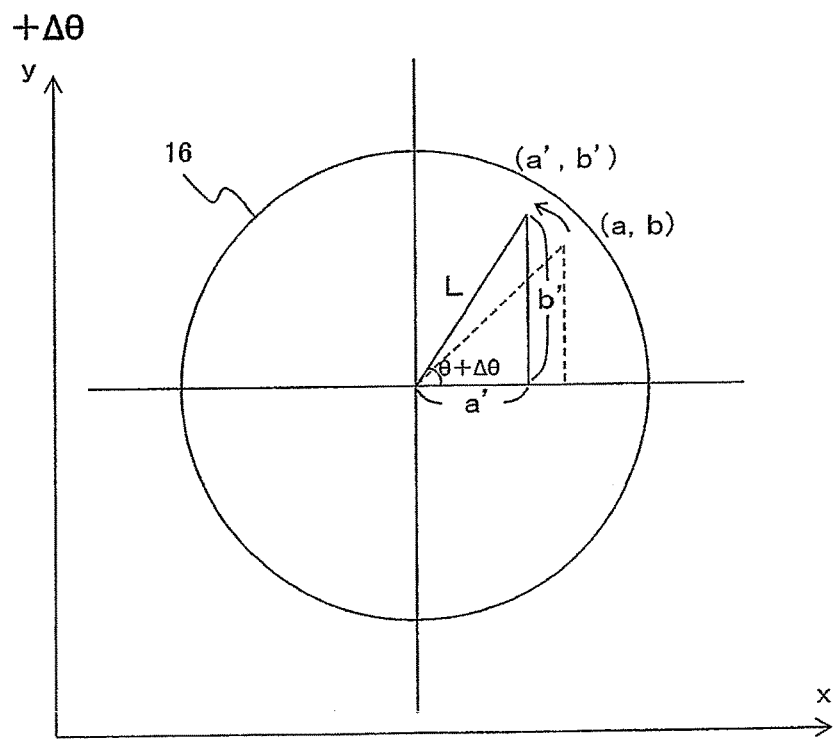

More specifically, when the rotary table 16 is intermittently rotated, the collaborative control is performed by a method shown in FIGS. 5A and 5B. That is, as shown in FIG. 5A, the coordinates (a, b) of the position that is set as the rotation center of the rotary table 16 are represented by the following equations:

$$a = L \cos \theta \quad (1),$$

and $$b = L \sin \theta \quad (2).$$

Here, assume a case where rotation by $\Delta\theta$ shifts the rotation center from (a, b) to (a', b'), as shown in FIG. 5B. In this case, the coordinates (a', b') are represented by the following equations:

$$a' = L \cos(\theta + \Delta\theta) \quad (3),$$

and $$b' = L \sin(\theta + \Delta\theta) \quad (4).$$

Thus, in order to bring the new position (a', b') back to the original position (a, b), "a" is shifted by $L \cos(\theta+\Delta\theta) - L \cos \theta$, and "b" is shifted by $L \sin(\theta+\Delta\theta) - L \sin \theta$.

Figure 6:
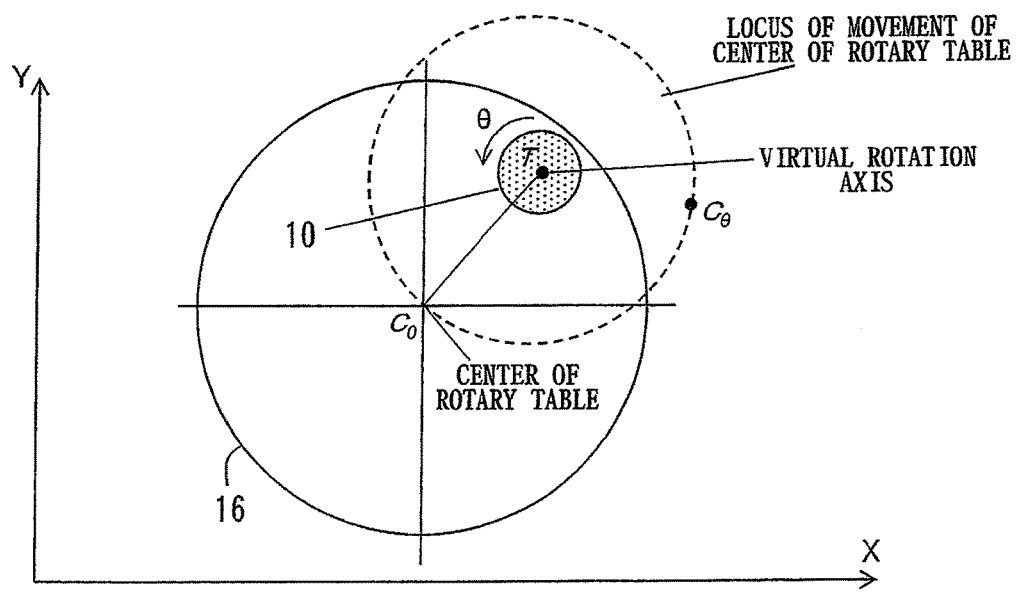
FIG. 6 is a schematic view showing a control method in a case where the embodiment performs continuous rotation.

Next, when the rotary table 16 is continuously rotated, a control method will be described with reference to FIG. 6. Assume a case where $C_0$ represents the center of the rotary table 16 at a rotation angle of 0° and an arbitrary position T on the rotary table 16 is set as a virtual rotation axis. In this case, a virtual rotation axis at the time of rotation by an angle θ about the virtual rotation axis T is realized as follows.

(1) A destination $C_\theta$ of the center of the rotary table 16 is calculated by the following equations using the center $C_0$ of the rotary table 16, the virtual rotation axis T, and the rotation angle θ:

$$\Delta_0 = T - C_0 \quad (5),$$

and $$C_\theta = T - R_\theta \Delta_0 \quad (6),$$

wherein, $R_\theta$ represents a rotation matrix.

(2) Then, by the collaborative control of rotary table shift axes, the center of the rotary table 16 is shifted from $C_0$ to $C_\theta$, while the rotary table is rotated by the rotation angle θ.

Figure 7:
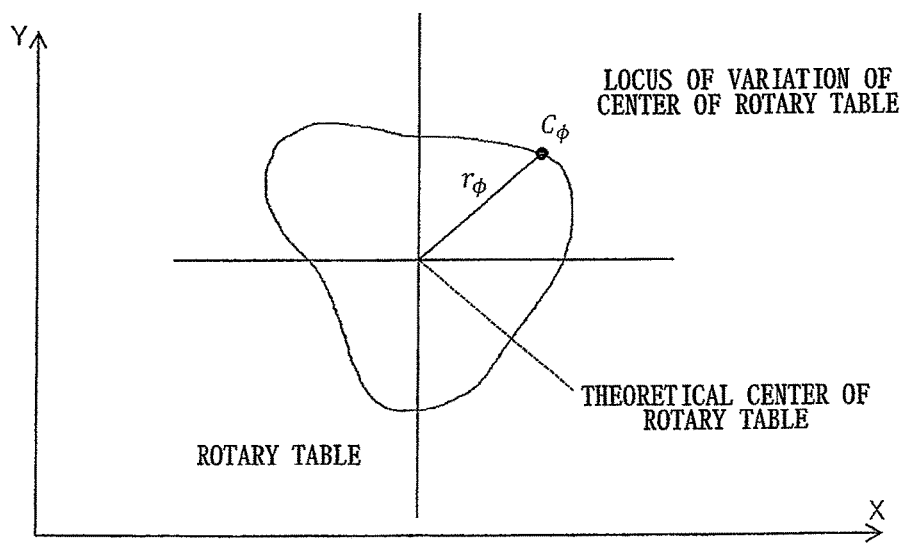
FIG. 7 is a schematic view showing a control method in a case where the embodiment corrects the eccentricity of a rotation axis.

It is noted that the center of the rotary table 16 (rotation axis) is not constant in position during rotation, but a variation caused by the eccentricity of the rotation axis necessarily occurs. FIG. 7 shows the locus of the variation of the center of the rotary table 16 during the rotation. $C_\phi$ represents the center of the rotary table 16 at a rotation angle θ.

Even with the eccentricity, the eccentricity of the rotation axis can be corrected in combination with the collaborative control of the virtual rotation axis by obtaining variation amounts (eccentric amounts) of the rotation axis in advance.

(1) First, an eccentricity correction table is produced in advance. To be more specific, the rotary table 16 is rotated at a constant angle pitch over 360° to measure the center $C_\phi$ of the rotary table 16 at every rotation angle φ.

The theoretical position of the center of the rotary table 16 is subtracted from each of the measured center positions $C_\phi$ to calculate an eccentric amount $r_\phi$. The eccentric amount $r_\phi$ of each rotation angle φ is recorded to make the eccentricity correction table 22.

FIG. 8 shows an example of the eccentricity correction table 22.

(2) Next, a destination $C_\theta$ of the center $C_0$ of the rotary table 16 is calculated, in the same manner as the method for realizing the vertical rotation axis.

(3) Next, an eccentric amount $r_\theta$ at the rotation angle θ is calculated by interpolating an eccentric amount in the eccentricity correction table 22.

(4) Next, a correction amount $E_\theta$ is calculated from the eccentric amount $r_\theta$ by the following equation:

$$E_\theta = (r_\theta \cos(\theta), r_\theta \sin(\theta)) \quad (7).$$

(5) Next, the destination $C_\theta$ of the center of the rotary table 16 is corrected on the eccentricity by the following equation, to calculate the center $C_{\theta'}$ of the rotary table 16 after the correction:

$$C_{\theta'} = C_\theta - E_\theta \quad (8).$$

(6) Next, the center of the rotary table 16 is shifted to $C_{\theta'}$ while the rotary table is rotated by the rotation angle θ, by the collaborative control of the rotary table shift axes.

This embodiment eliminates the need for moving the object to the center of the rotary table to obtain a high resolution tomographic image, and also eliminates the need for X-ray emission control and interlock control to open and lock an X-ray shield room associated with the movement of the object. Furthermore, if the rotary table has eccentricity that has been already known, the known eccentricity can be corrected by collaborative control considering the eccentricity at the time of the CT scan.

It is noted that the present invention is applied to the three-dimensional measurement X-ray CT apparatus in the aforementioned embodiment. The applications of the present invention are not limited to this, but the present invention is applicable to control for a rotary table in general apparatuses other than the three-dimensional measurement X-ray CT apparatus in a like manner. The method for correcting an eccentricity is not limited to that using the table, but the eccentricity may be corrected using a mathematical equation expressing the eccentricity, for example.

It should be apparent to those skilled in the art that the above-described embodiments are merely illustrative which represent the application of the principles of the present invention. Numerous and varied other arrangements can be readily devised by those skilled in the art without departing from the spirit and the scope of the invention.

The invention claimed is:

1. A method for controlling a rotary table for rotating an object disposed on the rotary table, the method comprising:
   intermittently rotating the rotary table by a minute angle;
   shifting the rotary table in a two-dimensional direction orthogonal to a rotation axis of the rotary table; and
   performing, using a processor, control of a shift position of the rotary table in the two-dimensional direction in synchronization with rotation of the rotary table, wherein rotation is made possible about a virtual rotation center that is set at an arbitrary position on the rotary table, the performing the control comprising:
      setting coordinates (a, b) of a position as a rotation center of the rotary table represented by a=L cos θ and b=L sin θ;
      moving the rotation center to a new position (a', b') with rotation of Δθ;
      shifting "a" by L cos(θ+Δθ)−L cos θ;
      shifting "b" is shifted by L sin(θ+Δθ)−L sin θ, in order to bring the new position (a', b') back to the original position (a, b); and
      correcting rotation eccentricity owing to eccentricity of the rotary table;
   producing an eccentricity correction table in advance;
   calculating a destination of the center of the rotary table;
   interpolating an eccentric amount in the eccentricity correction table to calculate an eccentric amount $r_\phi$ of a rotation angle φ;
   thereafter calculating a correction amount from the eccentric amount;
   correcting the destination of the center of the rotary table is corrected on the eccentricity;
   calculating a center $C_{\theta'}$ of the rotary table after the correction; and
   shifting the center of the rotary table to the center $C_{\theta'}$, while the rotary table is rotated by a rotation angle θ.

\* \* \* \* \*